United States Patent [19]

Dahlen et al.

[11] 4,442,833
[45] Apr. 17, 1984

[54] CASTING OR SPLINTING PACKAGE

[75] Inventors: Burton L. Dahlen, Benicia; L. John Odne, Walnut Creet; John D. Ryan, San Rafael, all of Calif.

[73] Assignee: Cutter Laboratories, Inc., Berkeley, Calif.

[21] Appl. No.: 248,610

[22] Filed: Mar. 27, 1981

[51] Int. Cl.³ .............................................. A61F 5/04
[52] U.S. Cl. .................................................. 128/90
[58] Field of Search ..................... 128/90, 89 R, 87 R; 206/389, 440

[56] References Cited

U.S. PATENT DOCUMENTS

| | | | |
|---|---|---|---|
| 3,314,419 | 4/1967 | Quick | 128/90 |
| 3,421,501 | 1/1969 | Beightol | 128/90 |
| 4,060,075 | 11/1977 | Blomer et al. | 128/90 |
| 4,108,169 | 8/1978 | Parker | 128/89 R |
| 4,193,395 | 3/1980 | Gruber | 128/90 |

FOREIGN PATENT DOCUMENTS 2651089 5/1978 Fed. Rep. of Germany .

OTHER PUBLICATIONS

3rd Annual Meeting–Society Biomaterials, presented 1977, Lysaught & Rich.

*Primary Examiner*—Benjamin R. Padgett
*Assistant Examiner*—T. J. Wallen
*Attorney, Agent, or Firm*—Theodore J. Leitereg; James A. Giblin

[57] ABSTRACT

A novel casting or splinting package is disclosed wherein a sheet comprising a textile substrate impregnated or coated with a water-curable resin system is non-sealably confined between a sheet of resilient, non-water-absorptive material and a sheet of flexible, non-water-absorptive material. The assembled sheets are enclosed in a porous envelope. In use, the casting or splinting package is immersed in water, squeezed to remove excess water, and then applied to and formed about the body part to be immobilized or supported whereupon the package becomes rigid.

16 Claims, 4 Drawing Figures

CASTING OR SPLINTING PACKAGE

BACKGROUND OF THE INVENTION

1. Field of the Invention

This invention relates to and has among its objects the provision of novel casting and splinting packages and novel methods for their construction. It is a particular object of the invention to provide a packaged casting or splinting material that may be immersed in water and then contacted with and formed about the body part to be immobilized or supported, whereupon it will become rigid and immobilizing or supporting in a short period of time. Further objects of the invention will be evident from the following description wherein parts and percentages are by weight unless otherwise specified.

2. Description of the Prior Art

Until recently, plaster of Paris casting materials have been employed almost exclusively in the orthopedic field to secure immobilization or support. However, polymeric resin casting materials have been disclosed in U.S. Pat. Nos. 3,373,741, 3,048,169, 3,630,194, 4,134,397, 4,214,578, and 4,231,356 and in German Patent Nos. 2,357,931 and 2,651,089. In usual practice a flexible carrier or substrate is coated or impregnated with a curable or settable composition, such as plaster of Paris or a polymeric resin. The substrate is selected generally from woven or knitted fabrics or non-woven webs made of natural or synthetic organic or inorganic fibrous materials. Strips of coated or impregnated substrates are activated and applied to the body part to be immobilized or supported after covering the body part with a soft cloth.

In U.S. Pat. No. 3,900,024 (hereinafter '024) there is disclosed an improved plaster cast and method of preparing it. In '024 a casting blank is prepared by placing a first sheet of deformable, water absorptive material on a supporting surface. A plurality of plaster splints are aligned on the above sheet. A second sheet of the same deformable, water-absorptive material as employed for the first sheet is placed over the first sheet to sandwich the plaster splints between the two sheets. The edge of the first and second sheets are bonded together to enclose the plaster splints therebetween. In use the '024 casting blank is saturated with water and then shaped about the body part to be immobilized or supported; securing means are used to hold the casting blank in place while it dries.

A plastic splint is disclosed in U.S. Pat. No. 3,373,741 (hereinafter '741). The '741 splint comprises a padded, sealed envelope containing at least two separate and distinct materials maintained separately. When the materials are mixed, a cured plastic resin composition is formed. In one embodiment of the '741 splint, the envelope also contains in a third compartment a reinforcing mat composed of a woven, knitted, or matted textile such as fiberglass, nylon, Dacron, cotton or Orlon. The lower portion of the envelope has a flexible pad secured thereto to prevent irritation of the patient and insulate the patient against heat liberated during the curing process. The flexible pad can be made of one-quarter inch polyurethane foam adhesively bonded to the envelope. The envelope can be formulated from a number of commercially available packaging films which are insoluble in, non-reactive with, and non-permeable to the uncured resin components. A polyester, epoxy, or polyurethane resin system may be used in the '741 splint.

In the use of the '741 splint, the separated components of the uncured resin system are mixed together while sealably confined in the envelope, and then the mixed components are contacted with the reinforcing mat in order to impregnate the mat. Next, the splint is placed in contact with the body part to be immobilized or supported and formed to the desired shape. The splint is held in place by means of straps or the like. Generally, the resin system will cure within ten minutes although longer times may occur depending on the resin system chosen.

Other casts and splints are disclosed in U.S. Pat. Nos. 3,656,475 and 3,674,021.

The known casting or splinting packages are disadvantageous because they are either cumbersome to manufacture or to apply or they are cumbersome to the patient who must wear the casting or splinting package.

SUMMARY OF THE INVENTION

The invention described herein provides novel casting or splinting packages and methods of making them. A first sheet of resilient, non-water-absorptive material is contacted with one or more second sheets comprising a textile substrate impregnated or coated with a water-curable resin system. A third sheet of flexible, non-water-absorptive material is disposed in overlying relationship to said second sheet containing the water-curable resin system and to said first sheet to non-sealably confine said second sheet between said first and third sheets. Said first, second, and third sheets then are enclosed in a porous envelope.

A primary advantage of the casting or splinting package of the invention is the ease with which it can be utilized. Simple immersion of the package in water followed by gentle squeezing is all that is necessary to place the package in a condition for contact with the body part to be immobilized to which it is secured by appropriate means. In a short period, e.g., less than fifteen minutes, depending on the type of water-curable resin system employed, the package becomes rigid. Thus, the casting or splinting package of the invention is particularly suited for use in emergency situations to achieve temporary immobilization or support. For instance, the instant package may be applied at the scene of an accident by a person having minimal training in such techniques. It is noteworthy that the casting or splinting package of the invention will obtain rigidity from the moisture in the air albeit much more slowly than if it is immersed in water.

Another advantage of the invention is the light weight of the package both in the uncured and the cured state. This feature of the present package is important because the package may be carried conveniently for use in emergency situations. Furthermore, the cured splint or cast is not cumbersome and permits freedom of movement for the injured patient other than for the immobilized body part.

Another advantage of the present invention is that the advantages of known polymeric resin systems as described hereinbelow are retained. Thus, the present casting or splinting packages have the following advantages:

1. The cured packages are highly permeable to X-rays so that X-ray photographs can be taken through the package without any shadow;
2. the packages required for producing a given supporting effect are much lighter than the known plaster of Paris materials providing the same effect, the saving in weight being up to about 80%;

3. the cured packages are resistant to water damage and may be exposed to water;

4. the cured packages have greater durability than their plaster of Paris counterparts;

5. no apparatus is required for applying the present packages; and 6. the packages of the invention set faster than conventional plaster of Paris splints.

A feature of the splint packages of the invention which contain polymeric resin disclosed in German Patent Nos. 2,357,931 or 2,651,089 is that they exhibit faster setting times than the casting materials disclosed in the aforementioned German Patents.

DESCRIPTION OF THE PREFERRED EMBODIMENTS

Figure 1:
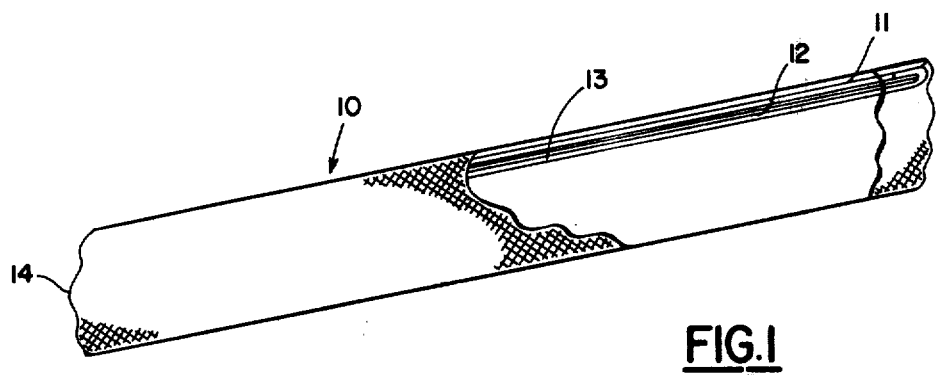
FIG. 1 is a perspective view of one embodiment of the invention.
Figure 2:
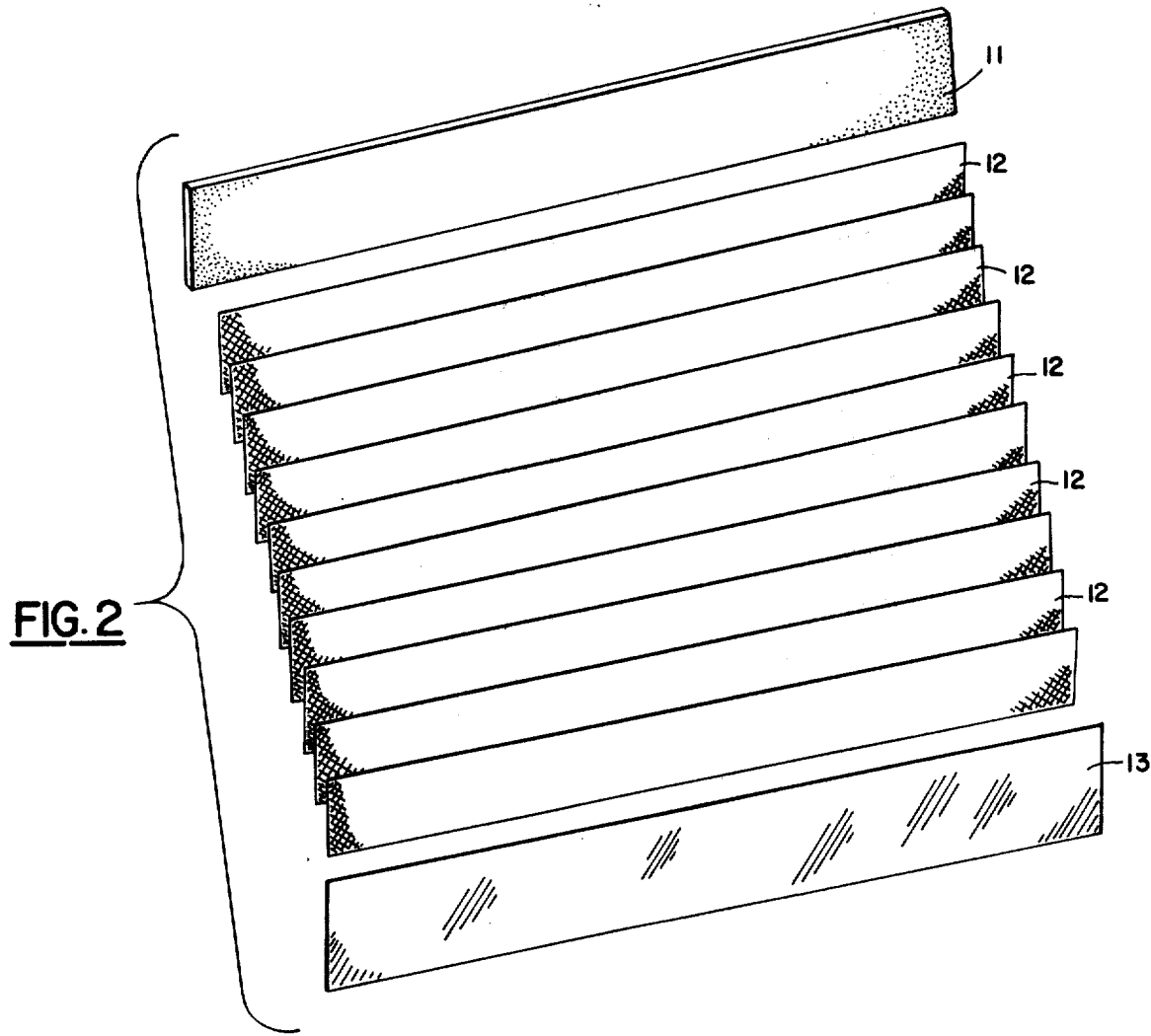
FIG. 2 is an exploded view of the embodiment of FIG. 1 without outside stockinette.

The invention will now be described in detail with reference to the accompanying drawings. In FIG. 2 first sheet 11 is composed of a resilient, deformable, non-water-absorptive material. By the term non-water-absorptive is meant that the material comprising sheet 11 has a closed cell structure, i.e., the pores of the cells of the foam are substantially non-interconnected. The cell pores in open cell foams are substantially interconnected. In the present invention 90% or more of the cell pores are not connected. Suitable materials for sheet 11, which must be non-reactive with the water-curable resin system of sheets 12, are closed cell foams of, for example, polyolefins such as polyethylene, polyesters, polyethers, silicones, neoprenes, polystyrenes, and the like. Closed cell polyurethane foams may be employed provided the cell structure of such foams is greater than 90% non-interconnected. The dimensions of sheet 11 (and package 10) are chosen generally to accomplish immobilization or support of the particular body part to be treated; the thickness of 11 is usually about 2–13 mm. A typical sheet 11 for immobilizing an arm, for example, will be about 76 cm. in length, 12 cm. in width, and 4 mm. thick. Sheet 11 must be sufficiently resilient and deformable to allow package 10 to be formed around the body part to be treated. Furthermore, sheet 11 must minimize heat transfer so that the heat formed during the curing of the polymeric resin will not cause burning of or discomfort to the person being treated. In addition, resilient sheet 11 provides a cushion for the body part in contact with the splint package and shields the skin from the polymeric resin.

Sheets 12 are placed in overlying relationship to sheet 11 and comprise a textile substrate impregnated or coated with a water-curable resin system which can become immobilizing or supporting when activated, within a time compatible with the conditions under which package 10 is used. Such textile sheets are known in the art. The term "textile substrate" is being used herein to include porous sheets of natural or synthetic materials such as woven or knitted fabric or non-woven webs made of natural or synthetic organic or inorganic fibrous materials such as, by way of example and not limitation, fibers of polyester, glass, cellulose, acrylic, polyamide, polyolefin, polyimide, wool, cotton, and the like and including blends thereof. Fibrous or filamentary strands or cables, braids, etc., are also suitable for use as substrates for sheets 12.

The textile substrates are impregnated or coated with a water-curable polymeric resin system. Any number of water-curable resin systems may be employed to coat or impregnate the above-described textile substrates. The important characteristics of the resin system employed are that it be non-toxic and water-curable, in other words, that it be activated by and subsequently obtain rigidity merely through the addition of water, whether directly by contact with water or indirectly by contact with a water- or moisture-containing material such as air. Examples of water-curable resin systems that may be employed in this invention are polyurethane resin systems, polyester resin systems, epoxy resin systems, acrylic resin systems, silicone resin systems, and so forth. Depending on the resin system chosen, the resin system may comprise the basic components from which the cured resin systems are formed or they may be a prepolymer or partial prepolymer system wherein the basic components are permitted to react, under controlled conditions, in advance. Resin systems which are suited to the present invention, by way of example without limitation, are disclosed in German Patent Nos. 2,357,931 (hereinafter '931) and 2,651,089 (hereinafter '089) and U.S. Pat. Nos. 4,214,578, 4,134,397, and 3,630,194 and 4,231,356.

Preferred water-curable resin systems in this invention are those polyurethane and silicone resin systems disclosed in '931. The reactive systems of '931 preferably contain less than about 1% by weight of volatile substances which can be removed by evaporation at 12 Torr (1 Torr is equal to 1 mm Hg) and 20° C. in one hour, but they are preferably still tacky and/or have a certain fluidity, shapeability, elasticity, pliability or plasticity so that the substrate impregnated with the reactive system will be in a workable state and have sufficient coherence. The reactive systems should not lose these properties when stored under moisture-free conditions, but on exposure to moisture, they should react to be converted into a rigid, non-tacky or only slightly tacky and no longer fluid and only slightly deformable state so that, for example, a structure made of several sheets 12 according to the invention will have sheets 12 adhering firmly to each other and will have a stabilized stiff and rigid character as in lamination.

The reactive systems of '931 are generally substances with a viscosity of from about 3,000 to 50,000 cP at 20° C. and, in this invention, from about 3,000 to 90,000 cP at 20° C. They contain reactive groups which, optionally in the presence of suitable accelerators or activators, react preferably at ambient temperatures with moisture to form a polymer network or at least undergo an increase in molecular size. These reactive groups may be, for example SiOR-groups or isocyanate groups, where R is a $C_1$–$C_{18}$ alkyl, $C_4$–$C_{18}$ cycloalkyl or a phenyl group.

One variation of this principle is represented by reactive systems which contain an accelerator or reactant which is masked or not effective on its own, but which reacts with moisture to be converted into an active form in which it is capable of undergoing the hardening reaction. Reactive systems of this kind include, for example systems which contain isocyanate groups and ketimines, the ketimines reacting with the moisture of the air to liberate a reactive amine.

The following are examples of classes of reactive substances suitable for the purpose of the invention which are sufficiently fluid in the absence of air:

A. silicones or other organic compounds with molecular weights of up to about 10,000 which contain SiOR-groups, where R is the same as defined immediately above which hydrolize on exposure to moisture, whereupon cross-linking or increase in molecular size occurs by condensation of the intermediately formed SiOH-groups;

B. polyisocyanates or compounds with viscosity below about 90,000 cP at 20° C., preferably polyesters, polyethers, polyamides, polyureas or polyurethanes, which are modified with isocyanate groups in end positions and/or side chains.

Compounds of type A have been described, for example, in German Offenlegungsschrift Nos. 2,155,258; 2,155,259 and 2,155,260, in German Patent Application No. P 22 43 628.8, and in U.S. Pat. Nos. 3,895,043 and 3,856,756, incorporated herein by reference. They are silyl substituted urea or biuret derivatives which can be prepared by reacting an aminoalkyl silane derivative, of the formula:

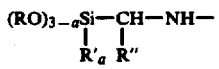

in which
R represents a $C_1$-$C_{18}$ alkyl or $C_4$-$C_{14}$ cycloalkyl group or a phenyl group,
R' represents a $C_1$-$C_{18}$ alkyl, $C_4$-$C_{10}$ cycloalkyl or $C_6$-$C_{10}$ aryl group which may be halogenated or cyano-substituted
R" represents a hydrogen atom or a methyl or phenyl group and
a=0, 1 or 2
with a compound which contains uretidone or isocyanate groups; or by reacting a compound of the general formula

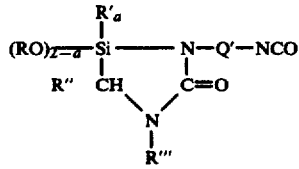

in which R, R', R" and a have the meanings specified above and R''' represent hydrogen or a $C_1$-$C_{18}$-alkyl, $C_4$-$C_{14}$-cycloalkyl or $C_6$-$C_{14}$-aryl or arylalkyl group with a higher molecular weight compound which contains hydroxyl or amino end groups.

The alkoxy silane derivatives used for the process according to the invention are preferably the mixtures described in German Offenlegungsschrift No. 2,138,943 and U.S. Pat. No. 3,793,253, incorporated herein by reference, because these can be applied solvent-free because of their viscous liquid consistency. The basic constituents of these mixtures are 5-silaimidazolidones-(2) of the formula

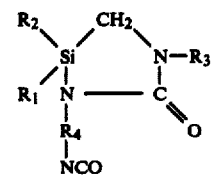

in which
$R_1$ and $R_2$ which may be the same or different, represent alkyl or alkoxy groups or may together represent a bisoxyalkylene group as described in U.S. Pat. No. 3,793,253,
$R_3$ represents hydrogen or an alkyl or aryl group and
$R_4$ represents a divalent (cyclo) aliphatic, araliphatic or aromatic group which may contain hetero atoms.

The compounds mentioned under B are preferably used in the present invention and may be either modified or unmodified polyisocyanates or preferably, reaction products of polyisocyanates with compounds which contain at least two hydrogen atoms that are reactive with isocyanates. Apart from compounds which contain amino, thiol or carboxyl groups, the compounds of this kind are preferably water and high-molecular weight or low-molecular weight polyhydroxyl compounds. Suitable higher molecular weight polyhydroxyl compounds are e.g. polyesters, polyethers, polythioethers, polyacetals, polycarbonates and polyester amides containing at least two, preferably two to four hydroxyl groups, of the kind known per se for the production both of homogeneous and of cellular polyurethanes.

Suitable polyester with hydroxyl groups are, for example, the reaction products of polyhydric, preferably dihydric alcohols to which trihydric alcohols may be added, and polybasic, preferably dibasic carboxylic acids. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic and/or heterocyclic and may be substituted, e.g., with halogen atoms and/or unsaturated. The following are mentioned as examples: succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride; endomethylene tetrahydrophthalic acid anhydride; glutaric acid anhydride; maleic acid; maleic acid anhydride; fumaric acid; dimeric and trimeric fatty acids such as oleic acid which may be mixed with monomeric fatty acids; dimethyl terephthalate and bis-glycol terephthalate. Suitable polyhydric alcohols are e.g. ethylene glycol; propylene-1,2- and -1,3-glycol; butylene-1,4- and -2,3-glycol; hexane-1,6-diol; octane-1,8-diol; neopentyl glycol; cyclohexane dimethanol (1,4-bis-hydroxymethyl cyclohexane); 2-methyl-propane-1,3-diol; glycerol; trimethylolpropane; hexane-1,2,6-triol; butane-1,2,4-triol; trimethylolethane; pentaerythritol; quinitol; mannitol and sorbitol; methyl glycoside; diethylene glycol; triethylene glycol; tetraethylene glycol; polyethylene glycols; dipropylene glycol; polypropylene glycols; dibutylene glycol and polybutylene glycols. The polyesters may contain a proportion of carboxyl groups in end positions. Polyesters of lactones such as ε-caprolactone or hydroxy carboxylic acids such as ω-hydroxycaproic acid may also be used.

The polyethers with at least two, generally two to eight, and preferably, two or three hydroxyl groups which may be used, are also known per se and may be prepared e.g. by polymerizing epoxides such as ethylene oxide, propylene, oxide, butylene oxide, tetrahydrofuran, styrene oxide or epichlorohydrin, each with itself, e.g. in the presence of boron trifluoride, or by their addition, either as mixtures or successively, to starting components which contain reactive hydrogen atoms such as water, alcohols or amines, e.g., ethylene glycol, propylene-1,3- or -1,2-glycol, trimethylolpropane, 4,4'-dihydroxy-diphenylpropane, aniline, ammonia, ethanolamine or ethylene diamine. Sucrose, polyethers such as those described e.g. in German Auslegeschriften Nos. 1,176,358 and 1,064,938 may also be used. Polyethers modified with vinyl polymers, as can be obtained e.g. by polymerizing styrene and acrylonitrile in the presence of polyethers (U.S. Pat. Nos. 3,383,351; 3,304,273; 3,523,093 and 3,110,695 and German Patent Specification No. 1,152,536) are also suitable as are also polybutadienes which contain hydroxyl groups.

Among the polythioethers, there should be particularly mentioned the condensation products of thiodiglycol with itself and/or with other glycols, dicarboxylic acids, formaldehyde, aminocarboxylic acids or amino alcohols. The products obtained are polythio mixed ethers, polythio ether esters or polythio ether esteramides, depending on the co-components.

Suitable polyacetals are, e.g., the compounds which can be prepared from glycols such as diethylene glycol, triethylene glycol, 4,4'-dioxethoxy-diphenyl dimethylmethane, hexanediol and formaldehyde. Polyacetals suitable for the purpose of the invention may also be prepared by polymerizing cyclic acetals.

Suitable polycarbonates with hydroxyl groups include those known per se which can be prepared by reacting diols such as propane-1,3-diol, butane-1,4-diol and/or hexane-1,6-diol, diethylene glycol, triethylene glycol or tetraethylene glycol with diaryl carbonates such as diphenyl carbonate or with phosgene. Suitable processes for preparing polycarbonates are taught in "Chemistry and Physics of Polycarbonates", by Hermann Schnell, Interscience Publishers, 1964.

Suitable polyester amides and polyamides include the predominantly linear condensates obtained from polyvalent saturated and unsaturated carboxylic acids or their anhydrides and polyvalent saturated and unsaturated amino alcohols, diamines, polyamines and mixtures thereof.

Polyhydroxyl compounds which already contain urethane or urea groups and modified or unmodified natural polyols such as castor oil, carbohydrates or starches may also be used. Addition products of alkylene oxides to phenol formaldehyde resins or urea formaldehyde resins are also suitable.

Other examples of higher molecular weight polyhydroxyl compounds may be found e.g. in High Polymers, Volume XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Höchtlen, Carl-Hanser-Verlag, Munich 1966, e.g. on pages 45 to 71.

Suitable low molecular weight polyhydroxyl compounds are, for example, the compounds mentioned above as suitable starting components for preparing the polyesters.

The polyisocyanates used as one-component reactive systems in the process according to the invention either as such or in the form of their reaction products with the above mentioned polyhydroxyl compounds may be aliphatic, cycloaliphatic, araliphatic, aromatic or heterocyclic. A detailed description of these polyisocyanates has been given by W. Siefken in Justus Liebigs *Annalen der Chemie,* Vol. 562, pages 75 to 136. The following are mentioned as examples; ethylene diisocyanate; tetramethylene-1,4-diisocyanate; hexamethylene-1,6-diisocyanate; dodecane-1,12-diisocyanate, cyclobutane-1,3-diisocyanate; cyclohexane-1,3- and 1,4-diisocyanate and any mixtures of these isomers; 1-isocyanato-3,3,5-trimethyl-5-isocyanatomethyl-cyclohexane (German Auslegeschrift No. 1,202,785); hexahydrotolylene-2,4- and -2,6-diisocyanate and any mixtures of these isomers, hexahydrophenylene-1,3- and/or -1,4-diisocyanate; perhydrodiphenylmethane-2,4' and/or -4,4'-diisocyanate; phenylene-1,3- and -1,4-diisocyanate; tolylene-2,4- and -2,6-diisocyanate and any mixtures of these isomers; diphenylmethane-2,4'- and/or -4,4'-diisocyanate; naphthylene-1,5-diisocyanate; triphenylmethane-4,4',4"-triisocyanate; polyphenyl-polymethylene polyisocyanates which can be obtained by aniline-formaldehyde condensation followed by phosgenation and which have been described e.g. in British Patent Specification Nos. 874,430 and 848,671; perchlorinated aryl polyisocyanates as described e.g. in German Auslegeschrift No. 1,157,601; polyisocyanates which contain carbodiimide groups as described in German Patent Specification No. 1,092,007; the diisocyanates described in U.S. Pat. No. 3,492,330; polyisocyanates containing allophanate groups according to British Patent Specification No. 994,890, Belgian Patent Specification No. 761,626 and published Dutch Patent Application No. 7,102,524; polyisocyanates which contain isocyanurate groups as described e.g. in German Patent Specification Nos. 1,022,789; 1,222,067 and 1,027,394 and in German Offenlegungsschriften Nos. 1,929,034 and 2,004,048; polyisocyanates containing urethane groups as described e.g. in Belgian Patent Specification No. 752,261 or in U.S. Pat. No. 3,394,164; polyisocyanates which contain acylated urea groups according to German Patent Specification No. 1,230,778; polyisocyanates which contain biuret groups as described e.g. in German Patent Specification No. 1,101,394; British Pat. No. 889,050 and French Patent Specification No. 7,017,514; the polyisocyanates prepared by telomerization reactions described e.g. in Belgian Patent Specification No. 723,640; polyisocyanates which contain ester groups such as those mentioned e.g. in British Patent Specification Nos. 956,474 and 1,072,956; U.S. Pat. No. 3,567,763 and in German Patent Specification No. 1,231,688 and reaction products of the above mentioned isocyanates with acetals according to German Patent Specification No. 1,072,385.

Particularly interesting for the process according to the invention are the non-volatile aliphatic and/or aromatic polyisocyanates or corresponding mixed types or various types of residue isocyanates obtained when commercial diisocyanates are processed by distillation. These products may, in addition, contain activators such as organometallic catalysts, for example, tin octoate and tertiary amines.

Polyisocyanates which are obtained by phosgenating aniline-formaldehyde condensates, by trimerizing polyisocyanates or by reaction of polyisocyanates with water or polyols under conditions which give rise to polyisocyanates with urethane, biuret, isocyanurate or allophanate structure are particularly preferred. In the process according to the invention, it is suitable to use mixtures of various such polyisocyanates because the various isocyanate components lower each other's melting points to form mixtures which are liquid at room temperature.

Particularly preferred in this invention are polyurethane resin systems disclosed in '089 (incorporated herein by reference). The isocyanate prepolymers of '089 suitable for impregnating the textile substrates mentioned above include, in particular, those which have from about 5 to 30% weight, preferably about 10 to 25% by weight, of aromatically bound isocyanate groups and about 0.05 to 2.5% by weight, preferably about 0.1 to 1.5% by weight, of tertiary amino nitrogen atoms. Furthermore, suitable choice of the viscosity of the starting materials used for preparing the isocyanate prepolymers ensures that the prepolymers have a viscosity of from about 5000 to 50,000 cP at 25° C.

The preparation of the isocyanate prepolymers is carried out in known manner by reacting excess quantities of aromatic polyisocyanates with polyols which contain tertiary amino nitrogen atoms, preferably at an isocyanate to hydroxyl (NCO/OH) ratio of between 2:1 and 15:1.

The aromatic polyisocyanates used may be any of the aromatic polyisocyanates known in polyurethane chemistry which have been described, for example, in "Polyurethanes, Chemistry and Technology", Part I, Interscience Publishers (1962) or in "Kunststoff-Handbuch", Volume VII, Polyurethane, Carl Hanser Verlag, Munich (1966). The following are preferred: 2,4-diisocyanatotoluene or 2,6-diisocyanatotoluene or isomeric mixtures thereof; 4,4'-diisocyanatodiphenylmethane and 2,4'-diisocyanatodiphenylmethane and mixtures of these isomers which may contain small quantities of 2,2'-diisocyanatodiphenylmethane, or any mixtures of the above mentioned polyisocyanates or polyisocyanate mixtures which can be obtained by the phosgenation of aniline-formaldehyde condensates and which contain higher nuclear diphenylmethane polyisocyanates in addition to 2,2'- 2,4'- and 4,4'-diisocyanatodiphenylmethane. The last mentioned diphenylmethane polyisocyanate mixtures are particularly preferred.

The following are examples of suitable polyols containing tertiary amino nitrogen atoms:

(1) Low molecular weight polyols having a molecular weight of from about 105 to 300 which contain tertiary nitrogen atoms and are free from ether groups, e.g. N-methyl-diethanolamine, N-ethyl-diethanolamine, N-methyl-dipropanolamine, triethanolamine or tripropanolamine;

(2) polyester polyols having a molecular weight of from about 300 to 2000, preferably about 800 to 1500, containing tertiary nitrogen atoms, which polyester polyols can be obtained by the reaction of polybasic acids with amino alcohols of the kind mentioned in (1) above as examples, if desired together with polyhydric alcohols which are free from nitrogen. Suitable polybasic acids include, for example, adipic acid, phthalic acid and hexahydrophthalic acid. Suitable nitrogen free polyhydric alcohols for the preparation of the polyesters include, for example, ethylene glycol, tetramethylene glycol, hexamethylene glycol and trimethylolpropane.

(3) Polyether polyols with tertiary amino nitrogen atoms having a molecular weight of from about 300 to 2000, preferably about 800 to 1500, which can be obtained in known manner by the alkoxylation of nitrogen containing starting compounds. Suitable starting compounds of this kind include, for example, ammonia, the amino alcohols mentioned in (1) above as examples and amines containing at least two-NH-bonds, e.g. ethylene diamine, aniline and hexamethylene-diamine. Suitable alkylene oxides for the preparation of the polyethers include, for example, ethylene oxide and propylene oxide. Propoxylation products of the above mentioned nitrogen containing starting materials are particularly preferred.

Any method may be used for coating and/or impregnating the textile substrates used in the process according to the present invention with the above mentioned water-curable polymeric resin systems. Conventional apparatus or devices may be used; for example, the textile substrates may be coated by means of doctor coat wipers or impregnated and subsequently squeezed off on rollers or centrifuged, or they may be sprayed with the resin system. The resin system may be used either solvent-free or as a solution. In the case of a solution, the preferred solvents are volatile solvents such as methylene chloride, acetone, methyl ethyl ketone, chloroform, tetrahydrofuran, ethyl acetate, chlorobenzene and dimethyl formamide. If auxiliary solvents have been used, the impregnated substrate is subsequently freed from them, for example, by a vacuum treatment.

Preferably the weight per unit area, density of mesh of the flexible support, and quantity of resin system applied within the ranges specified above are chosen so that only the fibers of the fabric become coated with the impregnating agent while gaps between the fibers are preserved to ensure the necessary porosity to air.

The impregnated or coated textile substrates may be colored, for example, by the addition of pigments or dyes to the isocyanate prepolymers. To increase the rigidity of the casting or splinting packages formed according to the invention, additives which may be chemically inert or capable of hardening under the action of water may be added to the resin system used for impregnating the textile substrates, but the use of such additives is generally unnecessary due to the excellent mechanical properties of sheets 12 obtained according to the above. Suitable additives would be, for example, chalk, glass or synthetic fibers, sand, mica, talc, carbon, or plaster of Paris.

The dimensions of sheets 12 should be compatible with that of the particular casting or splinting package. Generally, sheets 12 are each about 0.3–0.6 mm. thick and the number of sheets can vary depending on the particular end use of the product, usually about 5–20 sheets in most cases.

In a preferred embodiment package 10 further includes sheet 13 placed in overlying relationship to sheets 11 and 12 to non-sealably confine, i.e., to sandwich, sheets 12 between sheets 11 and 13. Sheet 13 comprises a flexible, deformable, non-water-absorptive, material. For example, sheet 13 can be a thin plastic film having the dimensions approximating sheet 11 except that 13 is usually about 0.02–0.15 mm thick. Generally, the length and width of 13 should be as great as or greater than that of sheets 11 and 12.

Any flexible film that is non-toxic, non-detrimentally-reactive with the water curable resin system, and meets the requirements for sheet 13 may be employed. Thus, one may use, for instance, films of polyolefins such as polyethylene, polypropylene, etc., polyesters, cellophane, cellulose acetate, polyvinylidine chloride, polyvinyl chloride, silicone, coated paper, Teflon and the like. By the term coated paper is meant paper coated to render it non-waterabsorptive, i.e., substantially unable to absorb an amount greater than that absorbed from air after dessication.

The sandwich formed from sheets 11, 12, and 13 is enclosed or sealably confined in porous, water-permeable envelope 14. Generally, 14 comprises a stockinette formed from woven or knitted fabric of natural or synthetic organic or inorganic materials such as those listed above for the textile substrate of sheets 12. Envelope 14 will come into direct contact with the body part to be treated and thus must be physiologically compatible therewith.

Casting or splinting package 10 is stored in sealed containers in the absence of moisture. They are preferably stored as rolls or folded flat in airtight metal containers, for example, aluminum containers. Sealed bags made of polyethylene coated aluminum foils or moisture sealed aluminum tins are particularly suitable for storing the packages according to the invention.

One of the advantages of the packages of the invention is that when packed airtight as described above they can be stored under normal conditions.

Figure 3:
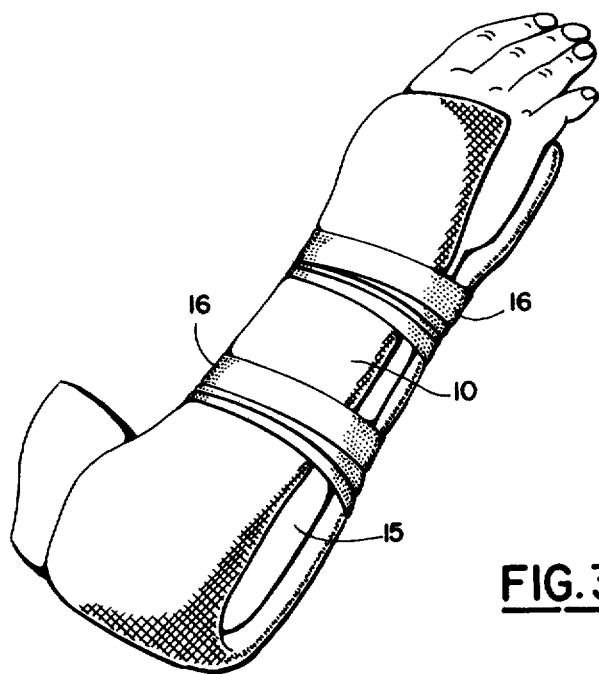
FIG. 3 is a perspective view of an embodiment of the invention in use to immobilize a forearm and wrist.
Figure 4:
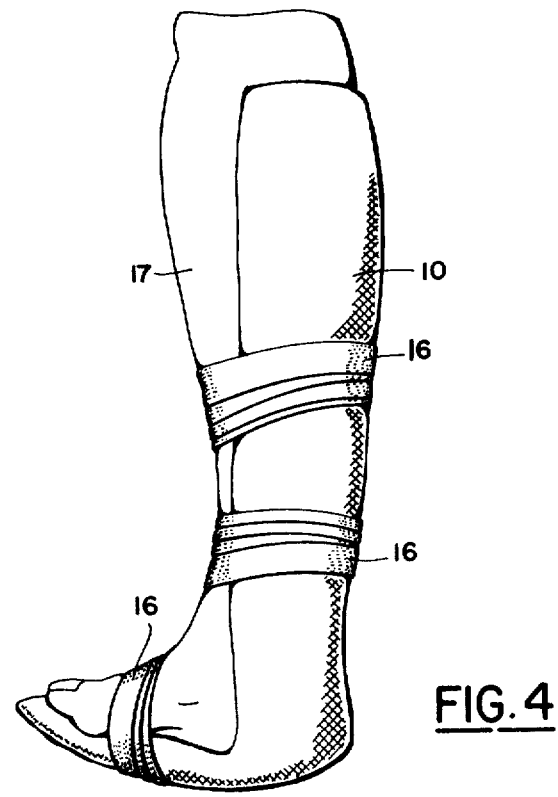
FIG. 4 is a perspective view of an embodiment of the invention in use to immobilize a foot and ankle.

In use package 10 preferably is immersed in water for about 30-90 seconds to activate the water-curable resin system on sheets 12. Package 10 is removed from the water and preferably squeezed gently to remove some of the water absorbed by envelope 14 thus leaving a sufficient, but not excessive, amount of water in package 10 to activate the resin system. Package 10 then, with sheet 11 toward the patient, is contacted with and formed around the body part under treatment, for example, arm 15 in FIG. 3 or leg 17 in FIG. 4. The so-formed package is held in place by retaining means 16 which may take the form of straps, tape, elastic or non-elastic bandages and the like. In the preferred embodiment of the invention the so-formed package will become immobilizing and supportive usually in less than about 20 minutes, generally about 5 to 15 minutes.

The success of the present invention is surprising and unexpected in view of the known casting or splinting packages. In particular U.S. Pat. No. 3,900,024 teaches the necessity of "sandwiching" plaster, or plaster-like splints, which will harden in the presence of water, between two sheets of deformable, water-absorptive material. We have found that our casting or splinting packages may be formed using sheets of a non-water-absorptive material to sandwich therebetween textile substrates impregnated or coated with a polymeric resin system that will harden in the presence of water. The advantage of our invention is that much less water is retained in the casting or splinting package after immersion in water. The resulting package is lightweight both during and after curing of the resin system, and will dry, i.e., lose its moisture, much more rapidly than a casting or splinting package with sheets 11 and/or 13 made of a water-absorptive material not in accordance with present invention.

EXAMPLE

The invention is demonstrated further by the following illustrative example.

Textile sheets impregnated with a water activated polyurethane prepolymer were prepared as described in German Patent No. 2,651,089. Each sheet was 38 cm long, 10 cm wide, and 0.4 mm thick. Ten sheets prepared as above were placed on top of a 0.4 mm thick polyethylene film which was 51 cm long and 11 cm wide. The approximately 6 cm of film extending beyond each end of the so-placed sheets was folded over the top of the sheets. Then, a piece of closed cell polyethylene foam about 41 cm long, 11 cm wide, and 3 mm thick was placed over the above sheets.

The above assembly was placed in a polyester knitted stockinette which previously had one end sewn shut and turned inside out. The open end of the filled stockinette was sewn together. The stockinette was marked to indicate the side to be placed next to the patient's skin, namely, the side containing the closed cell foam immediately next to the stockinette.

Splinting packages prepared according to the above procedure were sealed in laminated aluminum foil pouches to provide a water vapor barrier.

In use, the splinting package was immersed in water, kneaded repeatedly to ensure thorough wetting and then removed from water. The splint package was squeezed to express water from the stockinette covering and was placed on the patient with foam side against the skin. The splint package was molded to conform to the desired anatomical position. Wrinkles were smoothed and the splint was secured to the body with an elastic bandage. The splint became rigid in about seven minutes.

We claim:

1. A casting or splinting package for immersion in water and contact with and formation about a body part comprising -
    a first sheet of resilient, closed cell foam material,
    a plurality of second sheets comprising a textile substrate impregnated or coated with a water-curable resin system,
    a third sheet of a flexible material disposed in overlying relationship to said first sheet and said second sheets to non-sealably confine said second sheets between said first sheet and said third sheet, the third sheet being substantially unable to absorb an amount of water greater than that absorbed from air after desiccation, and
    a porous envelope wherein said first, second and third sheets are enclosed.

2. The package of claim 1 wherein the porous envelope is a stockinette.

3. The package of claim 1 wherein the resilient, non-water-absorptive material of said first sheet is a closed cell foam selected from the group consisting of polyolefins, polyesters, polyethers, silicones, neoprenes, polystyrenes, and polyurethanes.

4. The package of claim 1 wherein the flexible, material of said third sheet is a plastic film.

5. The package of claim 1 wherein the flexible material of said third sheet is a film selected from the group consisting of polyolefins, polyesters, cellophane, cellulose acetate, Teflon, polyvinylidine chloride, polyvinylchloride, and coated paper films.

6. The package of claim 1 wherein the textile substrate of said second sheet is a porous sheet of a natural or synthetic material.

7. The package of claim 1 wherein the textile substrate of said second sheet is slected from the group consisting of woven or knitted fabrics or non-woven webs made of natural or synthetic organic or inorganic fibrous materials.

8. The package of claim 7 wherein the natural or synthetic organic or inorganic fibrous materials are fibers selected from the group consisting of polyester, glass, cellulose, polyacrylic, polyamide, polyolefin, polyimide, wool, and cotton.

9. The package of claim 1 wherein the water-curable resin system of said second sheet is selected from the group consisting of polyurethane resin systems, polyester resin systems, epoxy resin systems, acrylic resin systems, and silicone resin systems.

10. The package of claim 1 wherein the water-curable resin system of said second sheet is a water-curable resin system prepolymer.

11. The package of claim 1 wherein the water-curable resin system of said second sheet is a reactive one-component system selected from the group consisting of
    (a) silicones and other organic compounds with molecular weights no greater than about 10,000 and containing SiOR-groups, where R is a $C_1$–$C_{18}$ alkyl, a $C_4$–$C_{14}$ cycloalkyl or a phenyl group,
    (b) ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3-diisocyanate, cyclohexane-1,4-diisocyanate, mixtures of cyclohexane-1,3- and -1,4-dissocyanate, 1-isocyanato-3,3,5-trimethyl-5-isocyanatomethylcyclohexane, hexahydrotolylene-2,4-diisocyanate, hexahydrotolylene-2,6-diisocyanate, mixtures of hexahydrotolylene-2,4- and -2,6-diisocyanate, hexahydrophenylene-1,3-diisocyanate, hexahydrophenylene-1,4-diisocyanate, mixtures of hexahydrophenylene-1,3- and -1,4-diisocyanate, perhydrodiphenylmethane-2,4'-diisocyanate, perhydrodiphenylmethane-4,4'-diisocyanate, mixtures of perhydrodiphenylmethane-2,4'- and -4,4'-diisocyanate, phenylene-1,3-diisocyanate, phenylene-1,4-diisocyanate, mixtures of phenylene-1,3- and -1,4-diisocyanate, tolylene-2,4-diisocyanate, tolylene-2,6-diisocyanate, mixtures of tolylene-2,4- and -2,6-diisocyanate, diphenylmethane-2,4'-diisocyanate, diphenylmethane-4,4'-diisocyanate, mixtures of diphenylmethane-2,4'- and -4,4'-diisocyanate, naphthlene-1,5-diisocyanate, triphenylmethane -4,4',4''-triisocyanate, polyphenyl-polymethylene polyisocyanates obtained by analine-formaldehyde condensation followed by phosgenation, perchlorinated aryl polyisocyanates, polyisocyanates containing carbodiimide groups, polyisocyanates containing allophanate groups, polyisocyanates containing urethane groups, polyisocyanates containing acylated urea groups, polyisocyanates containing biuret groups, polyisocyanates containing ester groups and the reaction products of the aforementioned polyisocyanates with compounds which contain at least two hydrogen atoms that are reactive with isocyanates selected from the group consisting of polyesters, polyethers, polythioethers, polyacetals, polycarbonates, polyurethanes, polyureas, and polyester amides.

12. The package of claim 1 wherein the water-curable resin system of said second sheet is an isocyanate prepolymer which contains free isocyanate groups and has been prepared from aromatic polyisocyanates and polyols containing tertiary amino nitrogen atoms, the prepolymer having an isocyanate content of about 5 to 30% by weight and a tertiary amino nitrogen content of about 0.05 to 2.5% by weight.

13. The package of claim 1 wherein the water-curable resin system of said second sheet becomes immobilizing or supportive, when activated, in a time compatible with the conditions under which the package is used.

14. The package of claim 1 wherein the water-curable resin system of said second sheet becomes immobilizing or supportive in less than about twenty minutes.

15. A method for immobilizing a body part, which comprises
    (a) activating the package of claim 1 in water,
    (b) forming the package about the body part to be immobilized, and
    (c) holding the package in place about the body part until the activated package becomes rigid and supportive.

16. A casting or splinting package for immersion in water and contact with and formation about a body part comprising
    a first sheet of closed-cell polymeric foam,
    a plurality of second sheets comprising a textile substrate impregnated or coated with an isocyanate prepolymer which contains free isocyanate groups and has been prepared from aromatic polyisocyanates and polyols containing tertiary amino nitrogen atoms, the prepolymer having an isocyanate content of about 5 to 30% by weight and tertiary amino nitrogen content of about 0.05 to 2.5% by weight,
    a third sheet of a flexible plastic film disposed in overlying relationship to said first sheet and said second sheets to non-sealably confine said second sheets between said first sheet and said third sheet, and
    a stockinette enclosing said first, second, and third sheets therein.

* * * * *